(12) United States Patent
Bengs et al.

(10) Patent No.: US 6,616,935 B1
(45) Date of Patent: Sep. 9, 2003

(54) METHOD OF FILTERING UV- LIGHT

(75) Inventors: Holger Bengs, Frankfurt (DE); Alfred Braunagel, Mainz (DE)

(73) Assignee: Celanese Ventures GmbH, Frankfurt am Main (DE)

( * ) Notice: Subject to any disclaimer, the term of this patent is extended or adjusted under 35 U.S.C. 154(b) by 0 days.

(21) Appl. No.: 09/869,220

(22) PCT Filed: Nov. 30, 1999

(86) PCT No.: PCT/EP99/09292

§ 371 (c)(1),
(2), (4) Date: Jun. 25, 2001

(87) PCT Pub. No.: WO00/38645

PCT Pub. Date: Jul. 6, 2000

(30) Foreign Application Priority Data

Dec. 28, 1998 (DE) .......................................... 198 60 370

(51) Int. Cl.$^7$ ............................ A61K 6/00; A61K 7/00; A61K 47/00; B01D 21/01

(52) U.S. Cl. ........................ 424/401; 514/778; 516/105

(58) Field of Search ......................... 424/401; 514/778; 516/105

(56) References Cited

U.S. PATENT DOCUMENTS

| 4,894,222 A | 1/1990 | Matravers | 424/59 |
|---|---|---|---|
| 4,971,723 A | * 11/1990 | Chiu | 516/105 |
| 5,256,404 A | 10/1993 | Martino et al. | 424/59 |
| 5,496,861 A | * 3/1996 | Rouse, 3 et al. | 514/778 |

FOREIGN PATENT DOCUMENTS

| EP | 0 487 000 A1 | 5/1992 |
|---|---|---|
| JP | 11246379 | 9/1999 |
| WO | WO 94/18932 | 9/1994 |

OTHER PUBLICATIONS

1995/883105, 1995, Japan, Abstract only.
"The Merck Index, Twelfth Edition", Merck Research Laboratories, 1996, p. 1502, left–hand column, paragraph 8954.
"New Polysaccharides Interest in Care Cosmetology", Pauly et al., In–Cosmetics 1997—Kongresszentrum Süd, Düsseldoef—Proceedings, pp. 417–444.
International Search Report in PCT/EP99/09292 dated Mar. 15, 2000.
International Preliminary Examination Report in PCT/EP99/09292 dated Mar. 28, 2001.

* cited by examiner

Primary Examiner—Theodore J. Criares
(74) Attorney, Agent, or Firm—Marshall, Gerstein & Borun

(57) ABSTRACT

The present invention relates to the utilisation of water-insoluble linear poly-α-glucan as UV filter, e.g., in sun protection products or in cosmetic as well as medical preparations. The invention also relates to a sun protection product which contains a biotechnically produced, water-insoluble linear poly-α-glucan as UV filter.

4 Claims, No Drawings

METHOD OF FILTERING UV- LIGHT

This is the U.S. national phase of International Application No. PCT/EP99/09292 filed Nov. 30, 1999, the entire disclosure of which is incorporated herein by reference.

The present invention relates to the use of water-insoluble linear poly-α-glucan as UV filter, and to a sun protection product comprising water-insoluble linear poly-α-glucan which has been produced biotechnologically.

Known UV filters are e.g. pigments, such as titanium dioxide and zinc oxide as such or in the form of "micronized particles".

From a cosmetics viewpoint, these pigments have the disadvantage that they whiten, i.e. make the skin appear white in color.

As a compromise for reducing the whitening to a tolerable degree and nevertheless achieving an acceptable UV protection, these pigments are usually used in sun protection products with a comparatively small particle size between 10 and 100 nm (A. Schrader, M. Rohr "Auffalligkeiten bei der Entwicklung und Prüfung von mikropigmenthaltigen Sonnenschutzformulierungen" [Unusual features in the development and testing of sun protection formulations containing micropigments] SÖFW Journal, 124, pages 478–487, 8/98).

In addition, titanium dioxide is to be viewed critically from a health viewpoint. In a study using titanium dioxide which had been extracted from sun protection products, it was observed upon irradiation with sunlight that titanium dioxide is able to catalyze photooxidation and damages bacterial DNA (CTFA/TRN Volume 12, No. 3, page 5 (1998) with reference to FEBS Letters, 418, 87–90, 1997).

A light-protecting action is also known for individual polysaccharides. For example, a light-protecting action has been described for poly-β-1,3-glucans (H. Eggensperger, M. Wilker, "Multiaktiv wirksame Polysaccharide Teil I-Pilzextrakte und Teil II-Pflanzliche Polysaccharide" [Multiactive polysaccharides part I-fungus extracts and part II-vegetable polysaccharides] in SÖFW Journal, 123, August 97, pages 542–546 and 12/97, pages 838–842). Poly-β-1,3-glucans which can be obtained from yeasts have a linear structure with a small proportion of β-1,6 branching.

It has also been proposed to use glycogen (a highly branched poly-1,4-α-glucan with branching in the 6-position) obtained biotechnologically or from marine molluscs for sun protection products (M. Pauly, G. Pauly "New Polysaccharides Interest in Care Cosmetology" IN-COSMETICS 1997, Conference Proceedings, pages 417–444, Verlag fur chemische Industrie, H. Ziolkowsky GmbH, 1998).

EP-B-0 487 000 proposes the use of a cosmetic composition in the form of an emulsion having 15 to 40% by weight of an enzymatically debranched starch in sun protection products, where the enzymatically degraded starch is a linear poly-1,4-α-glucan having 15 to 65 anhydroglucose units. However, there is no reference to a potential light protection action of the enzymatically debranched starch used therein; instead, it is used as an emulsifying auxiliary.

In view of the risks of intensive UV exposure, there is a growing need for suitable UV filters, preferably those which can reflect UV radiation, which not only offer reliable protection, but also do not impair the external appearance and are thus also suitable for daily use.

Surprisingly, it has been found that water-insoluble linear poly-α-glucan has a very good UV protective function, and upon application appears transparent and does not whiten.

The present invention thus relates to the use of water-insoluble linear poly-α-glucan as UV filter having an action which protects against UV radiation.

In a particularly preferred embodiment, the present invention relates to a sun protection product which comprises, as UV filter, water-insoluble linear poly-α-glucan which has been produced biotechnologically, in particular biocatalytically.

In principle, the water-insoluble linear poly-α-glucan can be added to any cosmetic or medicinal preparation for which a UV protecting action is desired. In particular, it is suitable for use in decorative cosmetics in order at the same time to impart to these a UV protecting action and to prevent, for example, skin aging as a result of intensive daily solar irradiation.

A preferred field of application is also sun protection products. The invention is described in more detail below using sun protection products as an example. However, it goes without saying that these statements are not limited to sun protection products, but can be applied directly to other fields of application for which UV protection is desired, such as the above-mentioned cosmetics.

Sun protection products containing water-insoluble linear poly-α-glucan prepared according to the invention can ensure excellent UV protection and appear transparent even when the concentrations of poly-α-glucan are high.

For the sun protection products or cosmetics prepared according to the invention by adding water-insoluble linear poly-α-glucans as UV filters, recourse may be made to the formulations and additives customary for such products. Particularly preferred bases for formulations are emulsions, such as, for example, W/O or O/W emulsions, aqueous or fat-containing gels, hydrogels, oils, emulsifier-free emulsions, wax-oil bases etc.

Examples of application forms are creams, compact creams, lotions, milks, masks, sprays, fluids, powders, ointments, ointment bases etc.

The sun protection products or cosmetics prepared according to the invention can, in addition to the water-insoluble linear poly-α-glucan, also comprise further, known UV filters.

The proportion of poly-α-glucan depends on the base used and is usually from about 0.5 to about 20% by weight, preferably about 2 to about 15% by weight, based on the total weight of the product. For many applications, an amount of about 10% by weight or less often suffices.

An amount of less than 0.5% by weight is of no importance for UV protection. If required, an amount greater than 20% by weight can also be used, for example amounts up to 70% by weight are incorporated for "sun protection cream compacts".

It goes without saying that the amount depends heavily on the composition of the respective product. If the product comprises further UV filters or if the base of the product is colored or pigmented per se, such as, for example, pigmented O/W or W/O emulsions, such that the UV permeability is reduced from the outset, smaller amounts of poly-α-glucan may be sufficient. For UV-permeable bases, e.g. transparent bases, such as nonpigmented emulsions, gels or oils, larger amounts of poly-α-glucan are advantageously added.

The required amount can, however, be determined directly from case to case by a person skilled in the art using a few routine experiments.

For the purposes of the present invention, water-insoluble linear poly-α-glucans are polysaccharides built up from glucans as monomeric building blocks such that the individual building blocks are always linked together in the same way. Each basic unit or building block defined in this way has exactly two linkages, each to one other monomer.

The only exceptions to this are the two base units which form the start and the end of the polysaccharide. These have only one linkage to a further monomer and form the endgroups of the linear polyglucan.

If the base unit has three or more linkages, then this is referred to as branching. In this context, the number of hydroxyl groups per 100 base units which are not involved in constructing the linear polymer backbone and form the branches gives the "degree of branching".

According to the invention, the linear water-insoluble poly-α-glucans have a degree of branching of at most 8%, i.e. they have a maximum of 8 branches and 100 base units. The degree of branching is preferably less than 4% and in particular at most 2.5%.

Particular preference is given to poly-α-glucans whose degree of branching in the 6-position is less than 4%, preferably at most 2% and in particular at most 0.5%, and is preferably in each case at most 2% and in particular 1% in the other positions, e.g. in the 2- or 3-position.

Particular preference is also given to poly-α-glucans with a degree of branching in the 6-position of less than 0.5%.

of particular suitability for the invention are poly-α-glucans which have no branches or whose degree of branching is so minimal that it is no longer detectable by traditional methods.

Examples of preferred water-insoluble linear poly-α-glucans are linear poly-α-D-glucans, the nature of the linkage being unimportant, provided there is linearity within the meaning of the invention. A particularly preferred example is poly-1,4-α-D-glucan.

For the present invention, the prefixes "α" or "D" refer solely to the linkages forming the polymer backbone and not to the branches. For the present invention, the term "water-insoluble poly-α-glucan" is to be understood as meaning compounds which, according to the definition of the German Pharmacopoeia (DAB=Deutsches Arzneimittelbuch, Wissenschaftliche Verlagsgesellschaft mbH, Stuttgart, Govi-Verlag, Frankfurt, [lacuna] edition, 1987), fall into the categories "slightly soluble", "sparingly soluble", "very sparingly soluble" and "virtually insoluble" compounds, corresponding to classes 4 to 7.

In the case of the polyglucans used according to the invention, this means that at least 98% of the amount used, in particular at least 99.5%, are insoluble in water under standard conditions (T=25° C.+/−20%, p=101325 Pascal+/−20%) (corresponding to classes 4 and 5, respectively).

For the present invention, preference is given to sparingly soluble to virtually insoluble compounds, in particular very sparingly soluble to virtually insoluble compounds.

"Very sparingly soluble" corresponding to class 6 can be illustrated by the following protocol: One gram of the polyglucan to be investigated is heated in 1 l of deionized water to 130° C. at a pressure of 1 bar. The solution which forms only remains stable briefly for a few minutes. Upon cooling under standard conditions, the substance precipitates out again. After cooling to room temperature and separation by means of centrifugation, at least 66% of the amount used can be recovered, taking into account experimental losses.

The poly-α-glucans used according to the invention may be of any origin provided the conditions given above with regard to the terms "linear" and "water-insoluble" are met.

They may have been obtained naturally or, in particular, by biotechnology methods. For example, they may be obtained from natural vegetable or animal sources by isolation and/or purification.

It is also possible to use sources which have been manipulated genetically such that they contain a higher proportion of unbranched or comparatively slightly branched polyglucans than the unmanipulated source.

They may have been prepared from non-linear polyglucans by enzymatic or chemical debranching. In this connection, non-linear polyglucans which contain branches may be treated with an enzyme such that cleavage of the branches arises, leaving, following removal of the branches, linear polyglucans. These enzymes may, for example, be amylases, isoamylases, gluconohydrolases, cyclomaltodextringlucanotransferases or pullulanases.

Biotechnology methods include biocatalytic, including biotransformation, or fermentation processes.

Linear poly-α-glucans prepared by biocatalysis (including: biotransformation) for the purposes of this invention means that the linear polyglucan is prepared by catalytic reaction of monomeric basic building blocks such as oligomeric saccharides, e.g. of monosaccharides and/or disaccharides, using a biocatalyst, usually an enzyme, under suitable conditions. In this connection, reference is also made to "in vitro biocatalysis".

Linear polyglucans from fermentations are, within the language usage of the invention, linear polyglucans which are obtained by fermentation processes using naturally occurring organisms, such as fungi, algae, bacilli, bacteria or protists or using non-naturally occurring organisms, but using natural organisms modified by genetic methods of the general definition, such as fungi, algae, bacilli, bacteria or protists, or which can be obtained with the use and assistance of fermentation processes. Reference is also made in this connection to "in vivo biocatalysis".

Examples of such microorganisms are Pichia pastoris, Trichoderma reseii, Staphyloccus carnosus, Escherichia coli and Aspergillus niger.

Advantageous processes for the biotechnological production are described, for example, in WO 95/31553 or the previously unpublished German patent application from the applicant with the official file reference 198 27 978.5.

According to WO 95/31553, amylosucrases are used for the preparation of linear poly-α-glucans, such as poly-1,4-α-D-glucan, by means of a biocatalytic process. Further suitable enzymes are polysaccharide synthases, starch synthases, glycol transferases, 1,4-α-D-glucan transferases, glycogen synthases and also phosphorylases.

It is also possible to use modified water-insoluble linear poly-α-glucans, it being possible for the poly-α-glucans to have been chemically modified, for example by esterification and/or etherification in one or more positions which are not involved in the linear linkage. In the case of the preferred 1,4-linked poly-α-glucans, the modification can take place in the 2-, 3- and/or 6-position.

For the purposes of the invention, modification means that the hydroxyl groups present which are not involved in the linkage are chemically changed. This excludes a ring opening of the glucan units, as occurs, for example, during oxidative carboxylation or hydrolysis. Measures for such modifications are sufficiently known to the person skilled in the art.

Thus, linear polyglucans, such as, for example, pullulans, which are per se water-soluble, can be made water-insoluble by modification. For the present invention, use is preferably made of water-insoluble linear polyglucans which have been prepared in a biotechnological process, in particular in a biocatalytic or a fermentation process, particular preference being given to biocatalytically prepared poly-α-glucan.

In contrast to poly-α-glucans which are isolated from natural sources, such as plants, the linear water-insoluble polyglucans obtained here have a particularly homogeneous property profile, e.g. with regard to the molecular weight distribution, they contain no, or at worst only very small amounts of, undesired byproducts, which have to be separated off at great expense or could lead to allergic reactions, and can be reproduced in a precisely specified manner in a simple way.

Although it is also possible to obtain comparatively homogeneous products using chemical or enzymatic debranching, in many cases a remainder of undebranched or only inadequately debranched starting material is left behind, which can only be separated off with difficulty.

Biotechnological and, in particular, biocatalytic methods have the advantage that water-insoluble linear poly-α-glucans, such as, for example, the preferred poly-1,4-α-D-glucans which contain no branches, or whose degree of branching is below the limit of detection using traditional analytical methods, can be obtained directly.

The poly-α-glucans can be used in the form of "alpha-amylase-resistant poly-α-glucans", as are described using the example of poly-1,4-α-D-glucan in the previously unpublished German patent application having the official file reference 198 30 618.0 from the applicant.

Alpha-amylase-resistant poly-α-glucans can be obtained by preparing a suspension or dispersion of water-insoluble polyglucans and water, heating the suspension or dispersion to a temperature in the range from 50 to 100° C., allowing the resulting paste-like mixture to cool to a temperature in the range from 50° C. down to the freezing point, preferably 35 to 15° C., 27 to 22° C., 16 to 0° C. or 6 to 2° C., over a period of from 1 to 72 h, preferably 1 to 36 h and in particular 15 to 30 h and retrograding the paste-like mixture at a temperature lower than the temperature of the heated paste-like mixture in a temperature range from 90 to 4° C., and, if desired, drying or dewatering the resulting product.

The poly-α-glucan can also be used as thermoplastic polyglucan obtainable by melting on linear water-insoluble polyglucan and adding at least 20% by weight, preferably at least 30% by weight, of a softener such as sorbitol, glycerol, condensation products and oligomers thereof, DMSO, succinic acid, citric acid monohydrate, malic acid, tartaric acid, etc. at about 170° C.

A description of suitable measures and properties of thermoplastic polyglucans using the example of the preferred linear water-insoluble poly-1,4-α-D-glucan is given in the previously unpublished German patent application having the official file reference 198 52 826, to which express reference is made here. To improve the incorporability, the thermoplastic poly-α-glucan can be granulated beforehand in a known manner.

The molecular weights $M_w$ (weight-average, determined by means of gel permeation chromatography relative to calibration with a pullulan standard) of the water-insoluble linear poly-α-glucans used according to the invention can vary within a wide range from $0.75 \times 10^2$ g/mol to $10^7$ g/mol. The molecular weight $M_w$ is preferably in a range from $10^3$ g/mol to $10^6$ g/mol and particularly preferably from $10^3$ g/mol to $10^5$ g/mol. A further advantageous range is from $2 \times 10^3$ to $8 \times 10^3$. Corresponding ranges apply to the preferably used poly-1,4-α-D-glucan.

The molecular weight distribution or polydispersity $M_w/M_n$ may likewise vary within wide ranges depending on the polyglucan preparation process. Preferred values are from 1.01 to 50, in particular from 1.01 to 15. Particular preference is given to polyglucans with low dispersity values, such as e.g. 1.01–2.5.

The polydispersity increases with a bimodal distribution of the molecular weights.

For the preparation of the sun protection products or other preparations, it is possible to use a single water-insoluble linear poly-α-glucan or a mixture of two or more thereof.

Due to their nature-identity, excellent biocompatibility can be expected for the water-insoluble linear poly-α-glucans used according to the invention.

The present invention is illustrated below by reference to individual examples.

EXAMPLE 1

In-vitro Production of Poly-1,4-α-D-glucan in a Biocatalytic Process Using Amylosucrase A sterilized (steam sterilization) 15 l vessel is charged with 10 l of a 20% strength sucrose solution. The enzyme extract, comprising amylosucrase, is added in one portion. The enzyme activity in this experiment is 16 units. The apparatus is provided with a likewise sterilized precision-ground glass paddle stirrer. The vessel is sealed and stored and stirred at 37° C. After a period of just a few hours, a white precipitate forms. The reaction is complete after a period of 180 hours. The precipitate is filtered off and, to separate off low molecular weight sugars, is washed five times with water. The residue which remains in the filter is dried at 40° C. in a drying cabinet with application of a vacuum using a membrane pump (Vacuubrand GmbH & Co., CVC 2). The mass is 685 g (yield 69%).

EXAMPLE 2

Characterization of the water-insoluble linear poly-1,4-α-D-glucan synthesized with amylosucrase from Example 1

2 mg of the poly-1,4-α-D-glucan from Example 1 are dissolved at room temperature in dimethyl sulfoxide (DMSO, analytical grade, Riedel-de-Haen) and filtered (2 μm filter). Some of the solution is injected into a gel permeation chromatography column. The eluent used is DMSO. The signal intensity is measured using an IR detector and evaluated against a Pullulan standard (Polymer Standard Systems). The flow rate is 1.0 ml per minute.

The measurement gives a number-average molecular weight ($M_n$) of 14,200 g/mol and a weight-average molecule weight ($M_w$) of 29,500 g/mol. This corresponds to a dispersity of 2.1.

EXAMPLE 3

Assessment of the Poly-1,4-α-D-glucan According to Example 1 as UV Filter

The assessment was carried out in accordance with the procedures of the COLIPA sun protection factor test method.

For the investigation, test persons were chosen who, in the distribution of their UV sensitivity, corresponded to the user majority, those acclimatized to UV were excluded.

Use was made of standard preparations P1 and P3 (Beiersdorf AG) compared with a preparation comprising 5% by weight of a water-insoluble linear poly-1,4-α-D-glucan as in Example 1.

The essential investigation parameters were:

Use of a Schrader sun simulator (SU 2000, manufacturer PTI-Photon Technology GmbH) which, with a 300 Watt xenon short-arc lamp, produces a light with a representative spectrum which was normalized to the intensity values of 320 nm.

The light beam from this lamp was directed using movable mirrors onto six points arranged in the shape of a cross such that homogeneous irradiation with 6 different light dosages was possible within one sitting. To exactly apply the amount of the light protection product required by the COLIPA standard of 2.0+/−0.04 mg/cm², the sun protection product was applied using a plastic syringe to a plastic spatula and was uniformly distributed using this spatula to the area to be irradiated.

The irradiation fields were read after 20 hours+/−4 hours.

The average sun protection factor (SPF) was calculated according to the following formula, where MED stands for minimum erythemal dose:

SPF (COLIPA) =MED (test field)/MED (empty field)

The average sun protection factor was 5.8 with a standard deviation of 0.7.

The confidence interval (CI95%) was within 20% of the average.

What is claimed is:

1. A method of filtering UV light from a surface, the method comprising the step of applying to the surface a topical preparation comprising a UV filter composition containing as an active ingredient a water-insoluble linear poly-1,4-α-D-glucan having a degree of branching of less than or equal to 0.5% and being substantially free of by-products and/or having a homogeneous molecular weight distribution.

2. The method of claim 1, wherein the topical preparation is selected from the group consisting of creams, compact creams, lotions, milks, masks, powders, ointments, ointment bases and soaps.

3. The method of claim 2, wherein the topical preparation is selected from the group consisting of creams, powders, and ointment bases for make-up.

4. The method of claim 3, wherein the make-up is blusher, eye shadow, or lipstick.

* * * * *